United States Patent [19]

Schultz

[11] 4,154,952

[45] May 15, 1979

[54] PROCESS FOR THE PRODUCTION OF SUBSTITUTED CYCLOPROPANE DERIVATIVES

[76] Inventor: Harry W. Schultz, 2137 NW. Robinhood Ave., Corvallis, Oreg. 97330

[21] Appl. No.: 766,801

[22] Filed: Jan. 31, 1977

[51] Int. Cl.$^2$ .................. C07C 69/74; C07C 69/76; C07C 121/46; C07C 121/60

[52] U.S. Cl. ............................. 560/96; 546/330; 546/335; 546/342; 260/346.11; 260/347.3; 260/347.4; 260/347.8; 260/464; 260/465 R; 260/465 D; 260/465 F; 260/465 G; 260/465 H; 560/37; 560/42; 560/51; 560/53; 560/59; 560/83; 560/102; 560/124

[58] Field of Search ............... 260/468 H, 464, 465 H, 260/295 R, 295 AM, 295.5 R, 294.9, 346.11, 347.4, 347.3, 347.8, 465 D, 465 G, 465 F; 560/124, 83, 59, 102, 42, 37, 53, 51, 96

[56] References Cited

U.S. PATENT DOCUMENTS

| | | | |
|---|---|---|---|
| 3,397,223 | 8/1968 | Payne | 260/468 H |
| 4,083,863 | 4/1978 | Brand | 560/86 |

OTHER PUBLICATIONS

Trost et al., *Sulfur Ylides,* Organic Chemistry, vol. 31, pp. 29-33 (1975).
March, *Advanced Organic Chemistry,* pp. 696-698 (1968).

*Primary Examiner*—Jane S. Myers
*Attorney, Agent, or Firm*—Eugene D. Farley

[57] ABSTRACT

Substituted cyclopropane derivatives are prepared in one step by interreacting an aldehyde, an active methylene compound, a sulfoxonium or sulfonium bromide or iodide, and a strong base in a reaction-inert organic solvent.

22 Claims, No Drawings

PROCESS FOR THE PRODUCTION OF SUBSTITUTED CYCLOPROPANE DERIVATIVES

BACKGROUND AND GENERAL STATEMENT OF THE INVENTION

This invention pertains to a process for the production of substituted cyclopropane derivatives.

Cyclopropane derivatives are compounds having important known and potential commercial applications. They are useful, for example, as insecticides, as ingredients of cosmetics, as pharmaceuticals, and in particular as tranquilizers. In addition, they are useful intermediates for the procedures of the synthetic organic chemical industry.

As is well known, substituted cyclopropanes are difficult of preparation. The prior art methods for their production have required two or more reactions using as starting materials compounds which themselves often are difficult of preparation. Yields have been correspondingly low.

Certain 1,1,2 substituted cyclopropane derivatives have been prepared heretofor using trimethylsulfoxonium iodide. In a procedure described by E. J. Corey and M. Chaykovsky, J. Amer. Chem. Soc., 87, 1353 (1965), trimethylsulfoxonium iodide was treated with sodium hydride to form dimethylsulfoxonium methylide and this reagent was reacted with alpha, beta-unsaturated ketone derivatives to form substituted cyclopropanes. Following this report, other investigators i.e. C. Kaiser, et al, J. Org. Chem. 30, 3972 (1965) and S. R. Landor and N. Punja, J. Chem. Soc. 2495 (1967), prepared 1,1,2 substituted cyclopropane derivatives by reacting dimethylsulfoxonium methylide with alpha, beta-unsaturated carboxylic acid derivatives.

Frequently, for use in the latter procedure the required alpha, beta-unsaturated carboxylic derivative is not readily available and must be prepared as a starting material. For this starting material, the involved reaction is often a condensation of the appropriate aldehyde and active methylene compound, followed by the isolation and the purification of the desired product.

The present invention is predicated on the discovery that a wide variety of cyclopropane products substituted in the 1, 2 and 3 positions may be produced in practical yields in reaction times in the order of one hour, or even less, and in a single reaction vessel by the interreaction of an aldehyde, an active methylene compound, a sulfoxonium or sulfonium bromide or iodide and a strong base, all dissolved in a reaction-inert organic solvent. The reaction product is a cyclopropane substituted in positions corresponding to the particular reagents employed.

The reaction takes place according to the following exemplary general equation, using trimethyl sulfoxonium iodide (where $R^4 = H$) and sodium hydride as an exemplary strong base:

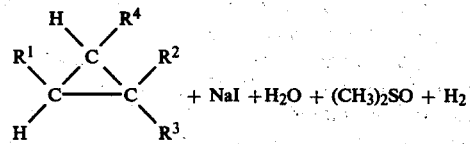

Without commitment to any particular theory, the mechanism for the above reaction is novel in that the reaction leads directly to the production of the substituted cyclopropane product. In particular, it is novel in that it does not involve the in situ formation of an intermediate alpha, beta-unsaturated carboxylic acid derivative.

As is well known, the conditions for the preparation of alpha, beta-unsaturated carboxylic acid derivatives generally require high temperature and longer reaction times than are used in the present invention (G. Jones, Organic Reactions, Vol. 15 p. 331-4 (1967). Furthermore, tests carried out by me using gas chromatography have failed to reveal the presence of any alpha, beta-unsaturated carboxylic acid derivatives in the substituted cyclopropane-yielding reaction mixtures employed in executing the process of my invention.

In addition, the reaction mechanism does not involve the formation of an intermediate epoxide derivative. While it is established, E. J. Corey and M. Chaykovsky, J. American Chemical Society 87, 1353 (1965), that aldehydes and dimethylsulfoxonium methylide react to form epoxides, it is further established, J. Org. Chem. 29, 2810 (1964), and also Bavin et al, J. Chemical Society 1964 p. 4535, that the addition of an active methylene compound to an epoxide does not produce cyclopropane derivatives. Accordingly, in the light of present knowledge, the hereindescribed reaction is totally new and does not follow the mechanism of any other reaction known to produce cyclopropane derivatives.

The procedure of my invention has many significant advantages.

It is a simple, one-step procedure. It is carried out in a very short reaction time. Readily available starting materials may be used in many instances. The reaction may be carried out in simple equipment at low temperatures. Super atmospheric pressures and the use of catalysts are not required. Practical yields of products are obtained. The procedure is versatile in that it may be directed to the production of a wide variety of cyclopropane derivatives substituted in the 1, 2 and 3 positions with selective constituent groups.

DESCRIPTION OF SPECIFIC EMBODIMENTS OF THE INVENTION

As noted above, the hereindescribed procedures for the production of substituted cyclopropane derivatives broadly involves the interreaction in a single step of an aldehyde, an active methylene compound, a sulfur-containing halide, specifically a sulfoxonium or sulfonium bromide or iodide and a strong base, all dissolved in a mutual reaction-inert organic solvent.

A wide variety of aldehydes $R^1CHO$ may be employed. Suitable aldehydes are those wherein $R^1$ is a member of the group consisting of hydrogen, an alkyl group having from 1 to 17 carbon atoms inclusive, phenyl, halophenyl, alkylphenyl having from 1 to 6 carbon atoms inclusive in the alkyl group, alkoxyphenyl having from 1 to 6 carbon atoms inclusive in the alkoxy group, pyridyl, and furfuryl.

Likewise, a wide variety of active methylene compounds $R^2CH_2R^3$ may be employed. Suitable ones are those wherein $R^2$ is carbomethoxy, carboethoxy, and nitrile, and wherein $R^3$ is phenyl, carbomethoxy, carboethoxy, nitrile, and amido.

A suitable sulfoxonium bromide or iodide comprises a compound in which $R^4$ is hydrogen. Suitable sulfonium bromides or iodides comprise compounds exemplified by carbethoxymethyl dimethylsulfonium bromide, methyl-(tetramethylene)-sulfonium iodide, or benzyl-(tetramethylene)-sulfonium bromide.

From a consideration of the equation given above for the reaction by which the substituted cyclopropanes are produced, it will be apparent that the sulfoxonium iodide employed determines the substituent in the number 1 position of the cyclopropane ring; the active methylene compound the substituents in the number 2 position of the cyclopropane ring, and the sulfoxonium iodide, the substituent in the number 3 position thereof.

Examples of suitable aldehydes for use in the reaction are:
  Benzaldehyde
  p-Chlorobenzaldehyde
  p-Methylbenzaldehyde
  p-Methoxybenzaldehyde
  Paraformaldehyde
  Acetaldehyde
  n-Butyraldehyde
  Dodecyl aldehyde
  2-Pyridincarboxaldehyde
  2-Furaldehyde Examples of suitable active methylene compounds for the present purposes are the following:
  Diethylmalonate
  Cyanoacetamide
  Ethylcyanoacetate
  Ethylacetoacetate Examples of sulfoxonium and sulfonium bromides and iodides suitable for the present purposes are the following:
  Trimethylsulfoxonium iodide
  Carbethoxymethyl dimethylsulfonium bromide
  Methyl-tetramethylene-sulfonium iodide
  Benzyl-tetramethylene-sulfonium bromide The fourth essential constituent of the reaction mixture is the strong base. By "strong" is meant one which is of sufficient strength to react with the sulfoxonium or sulfonium bromide or iodide, or the active methylene compound, as opposed to one added merely for the purpose of providing an alkaline reaction medium. The latter is of no consideration in any event, since the reaction is carried out in an organic solvent in the absence of water.

The strong base employed must be soluble in the organic solvent employed. Representative of such bases are sodium hydride, sodium methoxide, sodium ethoxide, potassium tertiary butoxide, sodium carbonate and potassium carbonate. A preferred strong base is sodium hydride.

The organic solvent employed in carrying out the reaction must be "reaction-inert". By this is meant, inert chemically to the active constituents of the reaction mixture. Additionally, it must be a mutual solvent for all of the reactants, including the strong base. Suitable solvents comprise dimethyl sulfoxide, dimethylformamide, tetrahydrofuran, benzene and ethanol. A preferred reaction-inert solvent is dimethylsulfoxide.

A sufficient amount of the solvent is employed to dissolve all of the reactants in the first instance and to maintain them in solution as the reaction progresses. As is indicated by an inspection of the equation representing the reaction, supra, the various reactants react mol for mol. Accordingly they preferably are employed in substantially equimolar proportions, by which is meant exactly equimolar proportions plus or minus about 0.50 mol. It will be understood that the reactants do not have to be exactly equimolar, since the reaction will proceed when one or more is present in excess. In this event the constituent in the lowest molar proportion will be the factor limiting the yield of cyclopropane product.

The reaction may be carried out at any temperature between just above the freezing temperature of the reaction mixture up to and including its boiling temperature. A suitable temperature range is from about 20° C. to about 100° C. In general, the character of the solvent will determine the actual temperature employed. As noted, however, it is a feature of the reaction that is proceeds rapidly and smoothly at relatively low temperatures, for example, temperatures in the range of from 20° C. to 60° C. In many instances the reaction can be carried out at ordinary laboratory or ambient temperatures.

The reaction conveniently is carried out in a reaction vessel fitted with a dropping funnel, a condenser with a drying tube attached, and suitable stirring or agitating means such as a magnetic stirring bar.

The order in which the various reagents are incorporated into the reaction mixture may be varied as follows, using trimethylsulfoxonium iodide and sodium hydride as illustrative starting materials.

Trimethylsulfoxonium iodide and sodium hydride first are reacted together in the inert solvent. To this is added a solution of the aldehyde and active methylene compound in the inert solvent.

The active methylene compound and sodium hydride first are reacted together in the inert solvent to form the sodium salt of the active methylene compound. To this is added trimethylsulfoxonium iodide, followed by the addition of a solution of the aldehyde in the inert solvent.

Trimethylsulfoxonium iodide and sodium hydride first are reacted together in the inert solvent. To this is added the active methylene compound followed by the addition of a solution of the aldehyde in the inert solvent.

The active methylene compound and sodium hydride are reacted together in the inert solvent to form the sodium salt of the active methylene compound. To this is added the aldehyde, followed by the addition of trimethylsulfoxonium iodide. Whatever the order of reagent addition, the reaction mixture is processed for product removal by solvent extraction. Preferably this is accomplished by cooling the reaction mixture, diluting it with water, and solvent extracting the cooled, diluted mixture with a suitable solvent for cyclopropane derivatives, such as diethyl ether.

The process of the invention is illustrated by the following examples:

EXAMPLE 1

To 1.0g of a 50% sodium hydride dispersion which had been previously washed with petroleum ether, was added 20 ml. dimethyl sulfoxide and 4.8 g trimethylsulfoxonium iodide. After stirring for ½ hour at room temperature a solution of 2.1 ml. benzaldehyde, 3.2 ml. diethylmalonate and 10 ml. dimethyl sulfoxide was added dropwise with stirring.

The mixture was stirred for ½ hour at room temperature, then one hour at 55°–60° C., diluted with 150 ml. water and extracted with ether. The ether extract yielded 1-phenyl-2,2-diethylcarboxylate cyclopropane (31% yield). The product was identified and the yield determined using a gas-liquid chromatography procedure based on comparison to an authentic sample of 1-phenyl-2,2-diethylcarboxylate cyclopropane.

EXAMPLE 2

To 0.1 g of 50% sodium hydride dispersion which was previously washed with petroleum ether, was added 4 ml. dimethyl sulfoxide and 0.3 ml. diethylmalonate. After stirring for 1½ hours at room temperature, 0.5 g. trimethylsulfoxonium iodide was added and the mixture stirred for 2 hours at room temperature. To this was added dropwise a solution of 0.4 ml. benzaldehyde in 1 ml. dimethyl sulfoxide while stirring.

After stirring for 16 hours at room temperature the mixture was diluted with 20 ml. water and extracted with ether. The ether extract yielded 1-phenyl-2,2-diethylcarboxylate cyclopropane (59% yield). The product was identified and the yield determined using a gas-liquid chromatography procedure based on a comparison with an authentic sample of 1-phenyl-2,2-diethylcarboxylate cyclopropane.

EXAMPLE 3

To 1 g. of 50% sodium hydride dispersion which was previously washed with petroleum ether, was added 40 ml. dimethyl sulfoxide and 5 g. trimethylsulfoxonium iodide. After stirring for ½ hour at room temperature, 3.2 ml. diethylmalonate was added in one portion while stirring and cooling in a cold water bath. The mixture was stirred for 3¼ hours at room temperature and to this was added dropwise while stirring a solution of 4.1 ml. p-methoxybenzaldehyde and 10 ml. dimethyl sulfoxide. The mixture was stirred an additional 16 hours at room temperature, diluted with 100 ml. water and extracted with ether. Distillation of the ether extract yielded 2.8 g. 1-p-methoxyphenyl-2,2-diethyl carboxylate cyclopropane. b.p. 155–165/2mm.

EXAMPLE 4

3.2 Ml. diethyl malonate was added dropwise to a stirred mixture of 1 g. of 50% sodium hydride dispersion, which was previously washed with petroleum ether, in 40 ml. dimethyl sulfoxide. After stirring for 1 hour at room temperature, 3 ml. n-butyraldehyde in 10 ml. dimethyl sulfoxide was added dropwise with stirring. After addition was complete, 5 g. trimethylsulfoxonium iodide was added. The mixture was stirred for 16 hours at room temperature, diluted with 100 ml. water and extracted with ether. Distillation of the ether extract yielded 1,1 diethylcarboxy-2-n-propyl cyclopropane, b.p. 145°–150°/2.1 mm.

EXAMPLE 5

To 0.1 g. of 50% sodium hydride dispersion which was previously washed with petroleum ether, was added 4 ml. dimethylsulfoxide and 0.5 g. trimethylsulfoxonium iodide. After stirring for 15 minutes at room temperature, 0.3 ml. diethylmalonate was added in one portion and stirred for one hour at room temperature and then a solution of 0.4 g. dodecyl aldehyde in 4 ml. tetrahydrofuran was added dropwise and stirred at room temperature for 6 hours followed by stirring at 60°–65° for 5 hours. The mixture was diluted with 10 g. ice-water and extracted with ether. The 1,1 diethylcarboxy-2-undecyl cyclopropane product was identified by gas chromatography and mass spectroscopy.

EXAMPLE 6

To 0.1 g. of 50% sodium hydride dispersion which was previously washed with petroleum ether, was added 4 ml. dimethyl sulfoxide and 0.5 g. trimethylsulfoxonium iodide. After stirring for 30 minutes at room temperature, 0.3 ml. diethylmalonate was added in one portion and stirred for 30 minutes at room temperature, and then a solution of 0.3 g. acetaldehyde (freshly distilled) in 1 ml. DMSO was added dropwise and stirred at room temperature for 16 hours followed by stirring at 55°–60° for 4½ hours. The mixture was diluted with 10 g. ice-water and extracted with ether. The product 1,1 diethylcarboxy-2-methyl cyclopropane was identified by gas chromatography-mass spectroscopy.

EXAMPLE 7

To 0.1 g. of 50% sodium hydride dispersion which was previously washed with petroleum ether, was added 4 ml. dimethyl sulfoxide and 0.5 g. trimethylsulfoxonium iodide. After stirring for 30 minutes at room temperature, 0.3 ml. diethylmalonate was added in one portion and stirred for 30 minutes at room temperature, and then 0.06 g. paraformaldehyde was added slowly, stirred at room temperature for 2 hours and then stirred at 55°–60° for 4 hours. The mixture was diluted with 10 g. ice-water and extracted with ether. The product was identified as 1,1-diethylcarboxy cyclopropane by gas chromatography-mass spectroscopy.

EXAMPLE 8

In like manner to Example 7, 0.1 ml. n-butyraldehyde was added as the aldehyde derivative, in place of the paraformaldehyde, to a solution of triethylsulfoxonium iodide, diethylmalonate, and sodium hydride in dimethyl sulfoxide. The reaction product was worked up in a similar manner. The product was identified as 1,1-diethylcarboxy-2-n-propyl cyclopropane by gas chromatography-mass spectroscopy.

EXAMPLE 9

In like manner to Example 7, 0.1 ml. benzaldehyde was added as the aldehyde derivative, in place of the paraformaldehyde, to a solution of trimethylsulfoxonium iodide, 0.2 g. cyanoacetamide, in place of the diethyl malonate, and sodium hydride in DMSO. The reaction product was worked up in a similar manner. The product was identified as 1-amido-1-cyano-2 phenyl cyclopropane by gas chromatography and mass-spectroscopy.

EXAMPLE 10

To 0.1 g. of 50% sodium hydride dispersion which was previously washed with petroleum ether was added 3 ml. dimethyl sulfoxide and a solution of 0.3 ml. diethylmalonate in 2 ml. dimethyl sulfoxide was added dropwise with stirring. After stirring for 15 minutes at room temperature, 0.5 g. of carbethoxymethyl dimethylsulfonium bromide was added in one portion and stirred at room temperature for 4 hours. The mixture was diluted with 10 g. of ice-water and extracted with ether. The product was identified as 1-phenyl-2,2,3-triethylcarboxy cyclopropane by gas chromatography and mass spectroscopy.

EXAMPLE 11

The following example illustrates the process of the invention using various aldehydes for the introduction of the indicated $R^1$ groups and the procedures of the indicated examples:

| Aldehyde Reactant | R¹ | Per Procedure of Example No. |
|---|---|---|
| Benzaldehyde | Phenyl | 1,2,9 |
| p-Chlorobenzaldehyde | p-Chlorophenyl | 2 |
| p-Methylbenzaldehyde | p-Methylphenyl | 2 |
| p-Methoxybenzaldehyde | p-Methoxyphenyl | 3 |
| Paraformaldehyde | Hydrogen | 7 |
| Acetaldehyde | Methyl | 6 |
| n-Butyraldehyde | n-Propyl | 4,8 |
| Dodecyl aldehyde | 2-Undecyl | 5 |
| 2-Pyridincarboxaldehyde | 2-Pyridyl | 2 |
| 2-Furaldehyde | 2-Furfuryl | 2 |

EXAMPLE 12

This example illustrates the process of the invention using various active methylene compound reactants for the introduction of the indicated $R^2$ and $R^3$ groups, using the procedure of the indicated example.

| Active Methylene Compound | $R^2,R^3$ | Per Procedure of Example No. |
|---|---|---|
| Diethylmalonate | Carboethoxy, carboethoxy | 1-8, 10 |
| Cyanoacetamide | Amido, nitrile | 9 |
| Ethylcyanoacetate | Ethylcarboxy, nitrile | 9 |
| Ethylacetoacetate | Acetyl, carboethoxy | 9 |

EXAMPLE 13

The following example illustrates the process of the invention using various sulfoxonium or sulfonium bromides or iodides for the introduction of the indicated $R^4$ groups and the procedures of the indicated examples:

| Sulfoxonium or Sulfonium bromide or iodide | $R^4$ | Per Procedure of Example No. |
|---|---|---|
| Trimethylsulfoxonium iodide | Hydrogen | 1-9 |
| Carbethoxymethyl dimethyl-sulfonium bromide | Ethylcarboxy | 10 |
| Methyl-tetramethylene-sulfonium iodide | hydrogen | 10 |
| Benzyl-tetramethyl-sulfonium bromide | Phenyl | 10 |

Having thus described my invention in preferred embodiments, I claim:

1. The process of making substituted cyclopropane derivatives which comprises:
   (a) forming a reaction mixture comprising:
   (1) an aldehyde of the general formula $R^1CHO$ wherein $R^1$ is a member of the group consisting of hydrogen, an alkyl group having from 1 to 17 carbon atoms inclusive, phenyl, halophenyl, alkylphenyl having from 1 to 6 carbon atoms inclusive in the alkyl group, alkoxyphenyl having from 1 to 6 carbon atoms inclusive in the alkoxy group, pyridyl, and furfuryl,
   (2) an active methylene compound of the general formula $R^2CH_2R^3$ wherein $R^2$ is a member of the group consisting of carbomethoxy, carboethoxy, and nitrile and $R^3$ is a member of the group consisting of phenyl, carbomethoxy, carboethoxy, nitrile, and amido, or $R^2$ is carboethoxy and $R^3$ is acetyl,
   (3) a sulfur-containing halide of the class consisting of $(R^4CH_2(CH_3)_2SOX$, $(R^4CH_2)(CH_3)_2 SX$ and $(R^4CH_2)(CH_2)_4 SX$ where $R^4$ is hydrogen, carbethoxy, or phenyl and X is a halide ion,
   (4) a substantially reaction-inert organic solvent for the said aldehyde, active methylene compound and sulfur-containing halide, and
   (5) a strong base soluble in the said organic solvent, and
   (b) interacting the constituents of the reaction mixture without distilling the same for substantial water removal thereby converting (them) the reactants to a substituted cyclopropane product of the formula

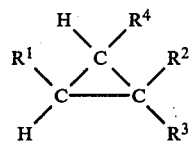

2. The process of claim 1 wherein the aldehyde comprises benzaldehyde.

3. The process of claim 1 wherein the aldehyde comprises p-chlorobenzaldehyde.

4. The process of claim 1 wherein the aldehyde comprises acetaldehyde.

5. The process of claim 1 wherein the aldehyde comprises dodecyl aldehyde.

6. The process of claim 1 wherein the aldehyde comprises 2-furaldehyde.

7. The process of claim 1 wherein the active methylene compound comprises diethylmalonate.

8. The process of claim 1 wherein the active methylene compound comprises cyanoacetamide.

9. The process of claim 1 wherein the active methylene compound comprises ethylcyanoacetate.

10. The process of claim 1 wherein the active methylene compound comprises ethylacetoacetate.

11. The process of claim 1 including the steps of forming the reaction mixture stepwise by first adding to the organic solvent the strong base, the sulfur-containing halide, and the aldehyde and thereafter adding the active methylene compound.

12. The process of claim 1 including the steps of first reacting the sulfur-containing halide with the active methylene compound in the organic solvent and in the presence of the strong base and thereafter adding the aldehyde and continuing the reaction for a time sufficient to produce the substituted cyclopropane derivative.

13. The process of claim 1 including the steps of reacting in the organic solvent the active methylene compound with the strong base, thereby converting it to the corresponding basic salt and thereafter adding the aldehyde and sulfur-containing halide and continuing the reaction for a time sufficient to produce the desired substituted cyclopropane product.

14. The process of claim 1 wherein there are employed substantially equimolar proportions of the aldehyde, active methylene compound, sulfur-containing halide, and strong base and wherein the reaction is carried out at a temperature of from just above the freezing temperature of the reaction mixture up to and including the boiling temperature thereof.

15. The process of claim 14 wherein the reaction temperature is from about 20 to about 100° C.

16. The process of claim 1 wherein the organic solvent is dimethylsulfoxide.

17. The process of claim 1 wherein the aldehyde is benzaldehyde, the active methylene compound is diethylmalonate, the sulfur-containing halide is trimethylsulfoxonium iodide, and the strong base is sodium hydride, the said reactants being employed in substantially equimolar quantities and the reaction being carried out at a temperature of from about 20° C. to about 100° C.

18. The process of claim 1 wherein the sulfur-containing halide is carbethoxymethyl dimethylsulfonium bromide.

19. The process of claim 1 wherein the sulfur-containing halide is methyl-tetramethylene-sulfonium bromide.

20. The process of claim 1 wherein the sulfur-containing halide is benzyl-tetramethylene-sulfonium bromide.

21. The process of making substituted cyclopropane derivatives which comprises:
(a) forming a reaction mixture comprising substantially equal molecular quantities of benzaldehyde, diethyl malonate, and a sulfur containing halide of the class consisting of (R⁴CH₂ (CH₃)₂SOX, (R⁴CH₂)(CH₃)₂ SX and (R⁴CH₂)(CH₂)₄SX where R⁴ is hydrogen, carbethoxy, or phenyl and X is a halide ion in the presence of a solvent comprising dimethyl sulfoxide and a strong base comprising sodium hydride, and
(b) interacting the constituents of the reaction mixture without distilling the same for substantial water removal thereby converting the reactants to a substituted cyclopropane product of the general formula

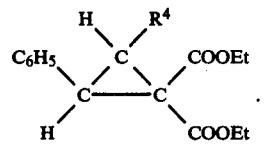

22. The process of claim 21 wherein the sulphur containing halide comprises trimethyl-sulfoxonium iodide.

* * * * *